(12) United States Patent
Basale et al.

(10) Patent No.: US 7,592,464 B2
(45) Date of Patent: *Sep. 22, 2009

(54) METHODS FOR PRODUCING AND PURIFYING 2-HYDROCARBYL-3,3-BIS(4-HYDROXYARYL)PHTHALIMIDINE MONOMERS AND POLYCARBONATES DERIVED THEREFROM

(75) Inventors: Rajshekhar Basale, Bangalore (IN); Hyacinth Mary Bastian, Goodwill Enclave (IN); Balakrishnan Ganesan, Karnataka (IN); Venkata Rama Narayanan Ganapathy Bhotla, Bangalore (IN); Gurram Kishan, Karnataka (IN); Pushpa Narayanan, Bangalore (IN); Swaminathan Shubashree, Bangalore (IN); Ravindra Vikram Singh, Utter Pradesh (IN)

(73) Assignee: SABIC Innovative Plastics IP BV, Bergen op Zoom (NL)

( * ) Notice: Subject to any disclaimer, the term of this patent is extended or adjusted under 35 U.S.C. 154(b) by 89 days.

This patent is subject to a terminal disclaimer.

(21) Appl. No.: 11/694,466

(22) Filed: Mar. 30, 2007

(65) Prior Publication Data

US 2008/0242873 A1 Oct. 2, 2008

(51) Int. Cl.
*C07D 209/44* (2006.01)
*C08G 64/00* (2006.01)
*C08G 63/02* (2006.01)

(52) U.S. Cl. .................. 548/482; 525/58; 525/125; 525/133; 525/176; 525/178; 525/433; 359/642; 548/471; 548/472

(58) Field of Classification Search .................. 548/482
See application file for complete search history.

(56) References Cited

U.S. PATENT DOCUMENTS

| | | | |
|---|---|---|---|
| 1,583,372 A | 5/1926 | Schudel | |
| 1,681,361 A | 8/1928 | Pasternak | |
| 1,940,146 A | 12/1933 | Roberts | |
| 1,940,495 A | 12/1933 | Hubacher | |
| 1,965,842 A | 7/1934 | Kranz | |
| 2,192,485 A | 3/1940 | Hubacher | |
| 2,522,640 A | 9/1950 | Martin | |
| 2,522,939 A | 9/1950 | Gamrath | |
| 4,217,438 A | 8/1980 | Brunelle et al. | |
| 4,252,725 A | 2/1981 | Prindle et al. | |
| 7,135,577 B2 | 11/2006 | Rai et al. | |
| 7,277,230 B2 | 10/2007 | Srinivasan et al. | |
| 2005/0222334 A1* | 10/2005 | Srinivasan et al. | 525/178 |
| 2005/0228137 A1 | 10/2005 | Srinivasan et al. | |
| 2006/0106234 A1 | 5/2006 | Tran-Guyon et al. | |
| 2007/0010619 A1 | 1/2007 | Chatterjee et al. | |

FOREIGN PATENT DOCUMENTS

| | | |
|---|---|---|
| EP | 1582549 | 10/2005 |
| WO | 2007064630 | 6/2007 |

OTHER PUBLICATIONS

International Search Report for International Application No. PCT/US2007/073966, mailed Feb. 7, 2008, 5 pages.
Written Opinion for International Application No. PCT/US2007/073966, mailed Feb. 7, 2008, 7 pages.
Fl. Ouiban, St. Oilianu and Sofia Toodorescu. "The Synthesis of Phenolphthalein with Chemistry". vol. 1958 9 p. 151-2, (1958).
Lin, M.S. and E.M. Pearce. "Polymers with Improved Flammability Characteristics. I. Phenolphthalein-Related Homopolymers", Journal of Polymer Science: Polymer Chemistry Edition, vol. 19, pp. 2659-2670 (1981).
Shuxian, Hu. "Study of the Preparation of Phenolphthalein Using Sulfonic Acid Type Cation Exchange Resin as Catalyst",Ion Exchange and Adsorption/Lizi Jiaohuan Yu Xifu, vol. 5(6), pp. 454-457 (1989).
Vaijula, Raghunadh, "Effect of Cation Exchange Resin in the Preparation of Phenolphthalein", Indian Journal of Technology, vol. 26, Oct. 1988, pp. 491-494.
Cillianu, et al, abstract of Romanian Patent No. 91178, published Mar. 30, 1987.
Fl. Ouiban, et al., abstract of "The synthesis of phenolphthalein with chlorosulfonic acid as the condensation agent", vol. 1958 9 p. 151-2, (1958).

* cited by examiner

*Primary Examiner*—Rebecca L Anderson
*Assistant Examiner*—Shawquia Young

(57) ABSTRACT

Disclosed herein is a method comprising reacting a phenolphthalein material and a primary hydrocarbyl amine in the presence of an acid catalyst to form a reaction mixture comprising 2-hydrocarbyl-3,3-bis(4-hydroxyaryl)phthalimidine, wherein the phenolphthalein material comprises greater than or equal to 99 weight percent phenolphthalein, based on the total weight of the phenolphthalein material; quenching the reaction mixture and treating the quenched reaction mixture to obtain a first solid. The first solid is purified by a combination of techniques to produce a solid comprising 2-hydrocarbyl-3,3-bis(4-hydroxyaryl)phthalimidine with sufficient purity to be used as a monomer in the synthesis of clear polymers.

27 Claims, No Drawings

METHODS FOR PRODUCING AND PURIFYING 2-HYDROCARBYL-3,3-BIS(4-HYDROXYARYL)PHTHALIMIDINE MONOMERS AND POLYCARBONATES DERIVED THEREFROM

BACKGROUND

Phenolphthalein derivatives have been used as aromatic dihydroxy compound monomers to prepare polycarbonate resins as well as polyarylate resins. Clear grade polycarbonates, which have high transparency and low haze values, are commercially desirable for making various useful articles. Coloration is not desirable for many commercial applications. Generally, high purity monomers are used as starting materials for making clear grade polycarbonates. Impurities in the monomer can result in polymers with undesirable properties such as discoloration or haze. Currently available methods to make and isolate phenolphthalein derivatives are lengthy and resource intensive. Accordingly, there remains an ongoing need for more efficient methods of making and isolating phenolphthalein derivatives—particularly those useful in making polymers for transparent applications.

BRIEF SUMMARY

Disclosed herein is a method comprising reacting a phenolphthalein material and a primary hydrocarbyl amine in the presence of an acid catalyst to form a reaction mixture comprising 2-hydrocarbyl-3,3-bis(4-hydroxyaryl)phthalimidine, wherein the phenolphthalein material comprises greater than or equal to 99 weight percent phenolphthalein, based on the total weight of the phenolphthalein material; quenching the reaction mixture and treating the quenched reaction mixture to obtain a first solution; filtering the first solution; adding 0.5 to 2.5 moles of a base per mole of the first solid to the filtered first solution to obtain a second solution; treating the second solution two or more times with a solid adsorbent to obtain a third solution; acidifying the third solution to precipitate a second solid; isolating and washing the second solid; triturating the second solid in a triturating solvent to obtain a third solid, wherein the third solid comprises greater than or equal to 99.9 weight percent 2-hydrocarbyl-3,3-bis(4-hydroxyaryl)phthalimidine, based on the total weight of the third solid; and wherein the 2-hydrocarbyl-3,3-bis(4-hydroxyaryl)phthalimidine is of formula (I):

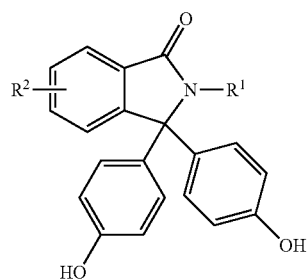

wherein $R^1$ is selected from the group consisting of a hydrogen and a hydrocarbyl group, and $R^2$ is selected from the group consisting of a hydrogen, a hydrocarbyl group, and a halogen.

Also disclosed is a method comprising reacting a phenolphthalein material and a primary hydrocarbyl amine in the presence of an acid catalyst to form a reaction mixture comprising 2-hydrocarbyl-3,3-bis(4-hydroxyaryl)phthalimidine, wherein the phenolphthalein material comprises greater than or equal to 99 weight percent phenolphthalein, based on the total weight of the phenolphthalein material; quenching the reaction mixture and treating the quenched reaction mixture to obtain a first solution; filtering the first solution; adding 0.5 to 2.5 moles of a base per mole of the first solid to the filtered first solution to obtain a second solution; treating the second solution two or more times with a solid adsorbent to obtain a third solution; acidifying the third solution to precipitate a second solid; isolating and washing the second solid; dissolving the second solid in a first solvent to obtain a fourth solution; treating the fourth solution with a solid adsorbent to obtain a fifth solution; removing the solvent from the fifth solution to obtain a third solid; triturating the third solid in a triturating solvent to obtain a fourth solid, wherein the fourth solid comprises greater than or equal to 99.9 weight percent 2-hydrocarbyl-3,3-bis(4-hydroxyaryl)phthalimidine, based on the total weight of the fourth solid; and wherein the 2-hydrocarbyl-3,3-bis(4-hydroxyaryl)phthalimidine is of formula (I). In some embodiments the fourth solid has less than or equal to 1 part by weight of sodium, iron or a combination of sodium and iron per million parts by weight of 2-hydrocarbyl-3,3-bis(4-hydroxyaryl)phthalimidine.

Also disclosed is a method comprising obtaining a first solution as described above; treating the first solution four or more times with a solid adsorbent to obtain a second solution; acidifying the second solution and heating the mixture at a temperature of 50 to 100° C. to precipitate a second solid; isolating the second solid; triturating the second solid in a triturating solvent to obtain a third solid, wherein the third solid comprises greater than or equal to 99.9 weight percent 2-hydrocarbyl-3,3-bis(4-hydroxyaryl)phthalimidine, based on the total weight of the third solid; and wherein the 2-hydrocarbyl-3,3-bis(4-hydroxyaryl)phthalimidine is of formula (I). In some embodiments the third solid has less than or equal to 1 part by weight of sodium, iron, or a combination of sodium and iron per million parts by weight of 2-hydrocarbyl-3,3-bis(4-hydroxyaryl)phthalimidine.

Also disclosed is a method comprising obtaining a first solution as described above; treating the first solution with a solid adsorbent four or more times to obtain a second solution; acidifying the second solution and heating at a temperature of 50 to 100° C. to precipitate a second solid; isolating the second solid; dissolving the second solid in a solvent to obtain a third solution; treating the third solution with a solid adsorbent to obtain a fourth solution; removing solvent from the fourth solution to obtain a third solid; triturating the third solid in a triturating solvent to obtain a fourth solid, wherein the fourth solid comprises greater than or equal to 99.9 weight percent 2-hydrocarbyl-3,3-bis(4-hydroxyaryl)phthalimidine, based on the total weight of the fourth solid; and wherein the 2-hydrocarbyl-3,3-bis(4-hydroxyaryl)phthalimidine is of formula (I). In some embodiments the fourth solid has less than or equal to 1 part by weight of sodium, iron or a combination of sodium and iron per million parts by weight of 2-hydrocarbyl-3,3-bis(4-hydroxyaryl)phthalimidine.

Methods of making polycarbonates comprising polymerizing the final solids obtained by the methods described above to form polymers are also disclosed.

DETAILED DESCRIPTION

Disclosed herein are methods of producing and purifying phenolphthalein derivatives that are suitable for use as monomers for preparing clear grade polymers, such as clear grade polycarbonates. An exemplary phenolphthalein derivative, 2-hydrocarbyl-3,3-bis(4-hydroxyaryl)phthalimidine is of formula (I):

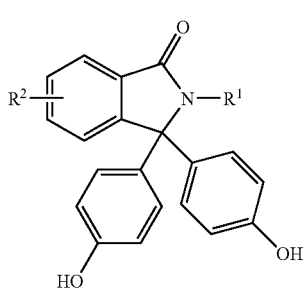

(I)

wherein $R^1$ is selected from the group consisting of a hydrogen and a hydrocarbyl group, and $R^2$ is selected from the group consisting of a hydrogen, a hydrocarbyl group, and a halogen.

The 2-hydrocarbyl-3,3-bis(4-hydroxyaryl)phthalimidine can be prepared by the reaction of a phenolphthalein material with a hydrocarbyl amine, such as, for example, an aromatic amine (also referred to herein as "aryl amine") of formula (II):

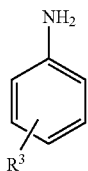

(II)

wherein $R^3$ is selected from the group consisting of a hydrogen, halogen and a hydrocarbyl group. The phenolphthalein material can comprise greater than or equal to 99 weight percent phenolphthalein, based on the total weight of the phenolphthalein material, of formula (III):

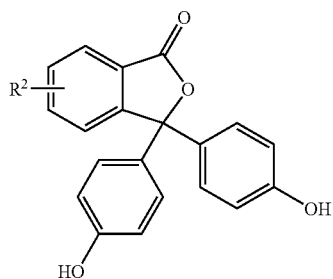

(III)

wherein $R^2$ is as defined above. In one embodiment, the phenolphthalein material comprises greater than or equal to 99.6 weight percent phenolphthalein.

For the purposes of this disclosure, the term "hydrocarbyl" is defined as a monovalent moiety formed by removing a hydrogen atom from a hydrocarbon. Representative hydrocarbyls include, but are not limited to, alkyl groups having 1 to 25 carbon atoms, such as methyl, ethyl, propyl, butyl, pentyl, hexyl, heptyl, octyl, nonyl, undecyl, decyl, dodecyl, octadecyl, nonadecyl, eicosyl, heneicosyl, docosyl, tricosyl, and the isomeric forms thereof; aryl groups having 6 to 25 carbon atoms, such as ring-substituted and ring-unsubstituted forms of phenyl, tolyl, xylyl, naphthyl, biphenyl, tetraphenyl, and the like; aralkyl groups having 7 to 25 carbon atoms, such as ring-substituted and ring-unsubstituted forms of benzyl, phenethyl, phenpropyl, phenbutyl, naphthoctyl, and the like; and cycloalkyl groups, such as cyclopropyl, cyclobutyl, cyclopentyl, cyclohexyl, cycloheptyl, cyclooctyl, and the like. The term "aryl" as used herein refers to various forms of aryl groups that have been described hereinabove for the "hydrocarbyl" group.

An acid catalyst can be used to facilitate formation of the phthalimidine product. Suitable acid catalysts include, but are not limited to, mineral acids such as hydrochloric acid (HCl), sulfuric acid, nitric acid, and phosphoric acid; weak inorganic acids such as boric acid, organic sulfonic acids such as methanesulfonic acid, Lewis acids such as stannic chloride, aluminum trichloride, ferric chloride, and zinc dichloride; sulfated zirconia; or combinations of two or more of the foregoing acid catalysts. Suitable acid catalysts also include amine salts of the above mineral acids. Examples of suitable amines include primary, secondary, and tertiary amines having any combination of aliphatic and aromatic groups bonded to the amine nitrogen. Suitable examples of amine salt catalysts include primary, secondary, and tertiary amine hydrochlorides. Hydrochloride salts of the primary aromatic amines of formula (II) are especially useful since the amines of formula (II) also serve as the starting material for preparing the phthalimidines of formula (I).

The catalyst can be introduced as a pre-formed salt into the reactor. Alternatively, the catalyst can be generated in the reactor by first charging an amine of formula (II) into the reactor and then adding ⅓ to 1 part by weight of an appropriate mineral acid to the reactor. In one embodiment, 0.1 to 0.3 part by weight of hydrogen chloride gas based on the total weight of the amine is introduced into a reactor charged with the amine to form an appropriate amount of the amine hydrochloride catalyst. More hydrochloric acid or more hydrogen chloride gas can also be used, but is generally not required. A solvent can optionally be employed to form the amine hydrochloride. The solvent can then be removed (if necessary), and the amine of formula (II) can be added, followed by addition of phenolphthalein (III).

The reaction of phenolphthalein (III) with the amine (II) proceeds by a condensation reaction to form the desired phthalimidine product (I). An excess of the amine over the phenolphthalein may be used to keep the reaction proceeding in the forward direction. Likewise, a higher reaction temperature with or without water by-product removal also facilitates product formation. However, in order to enhance the selectivity of 2-hydrocarbyl-3,3-bis(4-hydroxyaryl)phthalimidine (I), and suppress the formation of undesired by-product, for example, 2-hydrocarbyl-3,3-{(2-hydroxyaryl)(4-hydroxyaryl)}phthalimidine or 2-hydrocarbyl-3,3-{(4-hydroxyaryl)(4-aminoaryl)}phthalimidine, it is useful to control the temperature of the reaction mixture. The temperature of the reaction mixture is controlled such that the crude product is at least 97 weight percent, or more specifically, at least 98 weight percent, of 2-hydrocarbyl-3,3-bis(4-hydroxyaryl) phthalimidine. The chemical structures of the (2-hydroxyaryl)(4-hydroxyaryl)phthalimidine and (4-hydroxyaryl)(4-aminoaryl)phthalimidine by-products are shown in formulas (IV) and (V), respectively:

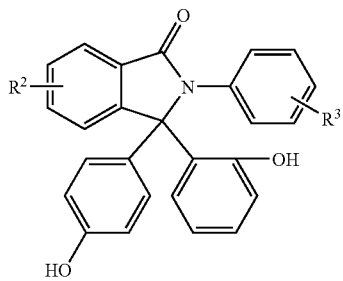

(IV)

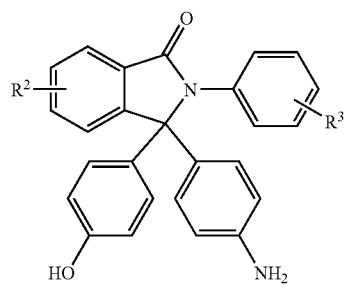

(V)

wherein $R^2$ and $R^3$ are as described above.

In one embodiment, the reaction temperature is controlled such that the water by-product (calculated based on the moles of the phenolphthalein (III) which is used as the limiting reagent) distills over a period of 8 hours to 50 hours, or more specifically, 12 hours to 24 hours. If the reaction mixture is heated such that the amount of water by-product distills within 6 hours, the phthalimidine product of formula (I) can have a relatively greater amount of the (4-hydroxyaryl)(4-aminoaryl)phthalimidine impurity shown in formula (V). Therefore, although a higher reaction temperature ensures a quicker consumption of the phenolphthalein (III) material, it also leads to formation of a higher amount of the impurity of formula (V). If the reaction temperature is not sufficiently high, a relatively large amount of the phenolphthalein material remains unreacted, thereby leading to an inferior product, e.g., forms colored byproducts during melt mixing, forms low molecular weight polymers, and the like. Thus, in one embodiment, the reaction mixture is heated to a temperature of 140° C. to 180° C. to remove water by-product and form the desired 2-hydrocarbyl-3,3-bis(4-hydroxyaryl)phthalimidine product. In another embodiment, the reaction mixture is heated to a temperature of 152° C. to 157° C. for 12 hours to 24 hours.

By way of example, phenolphthalein ($R^2$ is H in formula (III)) was reacted with aniline ($R^3$ is H in formula (II)) in the presence of hydrochloric acid as catalyst to form 2-phenyl-3,3-bis(4-hydroxyphenyl)phthalimidine (i.e., para,para-PP-PBP or "P,P-PPPBP""), as shown in formula (VI):

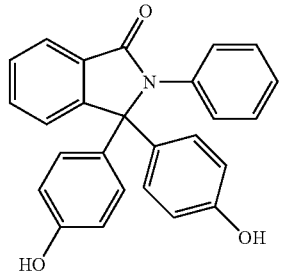

(VI)

Isolation of the desired phenolphthalein derivative from the reaction mixture includes quenching the reaction mixture and treating the quenched mixture to obtain a first solid. The reaction mixture can be quenched with an acid such as an aqueous mineral acid which precipitates a solid comprising 2-hydrocarbyl-3,3-bis(4-hydroxyaryl)phthalimidine and forms a slurry. An exemplary aqueous mineral acid is aqueous hydrochloric acid. Other suitable acids include, but are not limited to, sulfuric acid, boric acid, phosphoric acid, acetic acid, nitric acid, or combinations of two or more of the foregoing mineral acids; or combinations of two or more of the foregoing acids. The precipitate is isolated from the slurry. Suitable isolation methods include filtration, centrifugation and combinations thereof. The filtration can be conducted either at room temperature (about 25° C.) or at an elevated temperature of 25° C. to 90° C.

The precipitate can be washed with water to obtain a washed precipitate wherein the water has a temperature of 25 to 90° C., or more specifically, 35 to 80° C. The water wash is believed to remove inorganic salts and other water soluble impurities. The amount of water used per wash can be 5 to 15 milliliters (ml) per gram of the precipitate. The water wash step can be repeated several times, for example, 1 to 6 times. In some embodiments the water wash is repeated until the washed precipitate is chloride free as determined by suitable testing such as the silver nitrate test (i.e. chlorides give a white precipitate with silver nitrate—the water wash is tested for the presence of chloride).

The solid precipitate (first solid) is dissolved in a basic aqueous solution to obtain a first solution. Suitable basic aqueous solutions include inorganic basic solutions comprising an alkali metal or alkaline earth metal hydroxide, carbonate, or bicarbonate. Aqueous sodium hydroxide, for example, 4 wt. % NaOH aqueous solution, can be used. Suitable amount of the basic aqueous solution is 2 to 3 moles of the base per mole of the first solid.

Alternatively, the reaction mixture can be quenched with an aqueous base resulting in a biphasic mixture comprising a basic layer. Suitable aqueous bases include sodium hydroxide, potassium hydroxide, sodium carbonate, potassium carbonate and the like. Suitable amount of the basic aqueous solution is 2 to 3 moles of the base per mole of the product based on theoretical yield. An organic solvent is added to the biphasic mixture. Suitable organic solvents are those solvents in which the primary hydrocarbyl amine has good solubility and has little or no miscibility with the basic layer of the biphasic system. Exemplary solvents include ethylene dichloride, methylene dichloride, chloroform, ethyl acetate, and aromatic hydrocarbons such as toluene, xylene, cumene and benzene. It is also possible to use a mixture of solvents. The basic layer is separated from the biphasic system to obtain a first solution.

In one embodiment, the first solution can be filtered to remove any un-dissolved impurities. An extra amount of a base, for example, 0.5 to 2.5 moles of a base per mole of the first solid, is added to the first solution to obtain a second solution. Suitable bases for this purpose include solid alkali metal or alkaline earth metal hydroxide, carbonate, or bicarbonate. Solid sodium hydroxide is particularly useful. This extra base can help to remove impurities more efficiently and simplify the following purification steps.

The second solution is then treated with a solid adsorbent two or more times to obtain a third solution. Treating with a solid adsorbent comprises contacting the solution with the adsorbent followed by removing the adsorbent. Contact can be for 30 to 240 minutes at temperatures of 20° C. to 50° C. The solid adsorbent used in the first treatment may be the same type or a different type from the solid adsorbent used in the second treatment. Suitable first solid adsorbents include commercially available activated carbon, silica, and alumina. Contact with the activated carbon removes color-forming species and certain other impurities. Contact with silica can reduce the amount of metal ions such as iron, sodium or a combination thereof. Suitable activated carbon include, but are not limited to, the NORIT series of activated carbon available from Norit Corporation, and those activated carbons commercially available from E. Merck Company. Solid adsorbents can be recycled and reused. In some embodiments the activated carbon is derived from wood. In some embodiments, the amount of the solid adsorbents is 5 to 10 wt. % based on the weight of the dissolved solid per treatment cycle. Treatment with a solid adsorbent can be repeated up to 6 times.

In addition to functioning as a decolorizing agent, the activated carbon also aids in selectively adsorbing the 2-hydrocarbyl-3-{(4-hydroxyaryl)(2-hydroxyaryl)}phthalimidine isomeric impurity and also 2-hydrocarbyl-3-{(4-hydroxyaryl)(4-aminoaryl)}phthalimidine impurity.

After treatment with the adsorbent the resulting solution is acidified to pH 1.5 to 3.5, or more specifically, pH 2 to 3, with an aqueous mineral acid, such as aqueous hydrochloric acid, to precipitate a second solid. The aqueous mineral acid can have a concentration of 3 to 10 weight percent (wt. %), or more specifically, 4 to 6 wt. %. As used herein, the weight percentage of aqueous mineral acid is based on the weight of the aqueous mineral acid in solution. For example, a 5 wt. % HCl aqueous solution contains 5 wt. % of HCl and 95 wt. % of water. The acidifying step can be carried out at a temperature of 25 to 80° C. for a time of 1 to 4 hours. In one embodiment, the acidifying step is carried out at an ambient temperature of about 25° C. In another embodiment, the acidifying step is carried out at a temperature of 25 to 80° C. Acidification at a higher temperature can help to remove impurities like metals, for example iron and sodium. After acidification a precipitate (the third solid) forms and the solid is then isolated.

The second solid is then triturated in a triturating solvent to obtain a third solid. As used herein, "triturating" is defined as mixing a solid with a triturating solvent and then isolating any undissolved material by filtration, centrifugation, or a combination thereof. The triturating solvent is typically chosen such that the desired product has a low solubility in the solvent. During trituration, some or all of the solid such as impurities may dissolve in the solvent. The exact amount of the dissolved material depends on, among other things, the temperature at which the trituration and subsequent filtration is conducted, the type of solvent used, and the amount of solvent used.

Trituration can be conducted at a temperature above the freezing point of the trituration solvent and less than or equal to the boiling point of the trituration solvent. For example, trituration can be conducted at a temperature of 5 to 70° C. The time required for trituration varies depending on the trituration system and conditions and can be 5 minutes to 4 hours. Trituration can occur more than once and each trituration may use the same or different trituration solvents.

Suitable triturating solvents include, but are not limited to, polar solvents, non-polar solvents, and combinations of two or more of the foregoing solvents. Exemplary polar solvents include, but are not limited to, methanol, ethanol, isopropanol, propanol, chloroform, acetone, ethyl acetate, phenol, water, aqueous acidic solutions, and combinations of two or more of the foregoing.

Exemplary non-polar solvents include, but are not limited to, aromatic hydrocarbons having 6 to 14 carbons, aliphatic hydrocarbons having 5 to 8 carbons, non-polar chlorinated hydrocarbons, and combinations of two or more of the foregoing. Non-limiting examples of suitable aromatic hydrocarbon solvents include toluene, xylene, cumene, benzene and the like. Non-limiting examples of suitable aliphatic hydrocarbon solvents include hexane, cyclohexane, pentane, and the like. Non-limiting examples of non-polar chlorinated hydrocarbon solvents include 1,2-dichloroethane and the like.

Non-limiting examples of suitable triturating solvents comprising mixtures include methanol:toluene, methanol:water, ethyl acetate:toluene, ethyl acetate: 1,2-dichloroethane, acetone: 1,2-dichloroethane, acetone:toluene, acetone:hexane, isopropanol:toluene, acetone:water, and isopropanol:water. The volume ratios (v:v) of the solvent mixtures can be 1:99 to 99:1. Exemplary solvent mixtures include, but are not limited to, methanol:toluene (2:98, v:v), methanol:toluene (13:87, v:v), and methanol:water (90:10, v:v).

In a second embodiment, the second solid is obtained as discussed above. The second solid is then dissolved in a solvent to obtain a fourth solution. Suitable solvents include, but are not limited to, aqueous alcohols, aqueous acetone, a mixture of an alcohol and a ketone, aqueous amides, aqueous dimethylsulfoxide, and combinations of two or more of the foregoing solvents. In one embodiment, the first solvent comprises isopropanol.

The fourth solution is then treated with a solid adsorbent as described above to obtain a fifth solution and the solvent is removed from the fifth solution to obtain a third solid.

The third solid is then triturated as described above to obtain a fourth solid, wherein the fourth solid comprises greater than or equal to 99.9 weight percent 2-hydrocarbyl-3,3-bis(4-hydroxyaryl)phthalimidine of formula (I), based on the total weight of the fourth solid.

In a third embodiment, the first solution (obtained as described above) is contacted with a solid adsorbent four or more times to obtain a second solution. The above treatment with a solid adsorbent can be repeated up to 6 times. The second solution is then acidified to pH 1.5 to 3.5, or more specifically, pH 2 to 3, with an aqueous mineral acid, such as aqueous hydrochloric acid, at a temperature of 50 to 100° C., or more specifically, 60 to 70° C., to precipitate a second solid. Suitable acids and acidifying conditions are the same as those described above in the first embodiment. The second solid is then isolated.

The second solid is then triturated as described above to obtain a third solid wherein the third solid comprises greater than or equal to 99.9 weight percent 2-hydrocarbyl-3,3-bis (4-hydroxyaryl)phthalimidine of formula (I), based on the total weight of the third solid.

In a fourth embodiment, the first solution is treated with a solid adsorbent four or more times to obtain a second solution. The first solution can be treated up to 6 times. The second solution is then acidified to pH 1.5 to 3.5, or more specifically, pH 2 to 3, with an aqueous mineral acid, such as aqueous hydrochloric acid, at a temperature of 50 to 100° C., or more specifically, 60 to 70° C., to precipitate a second solid. Suitable acids and acidifying conditions are the same as those described above in the first embodiment. The second solid is then isolated.

The second solid is then dissolved in a first solvent to obtain a third solution. Suitable first solvents include, but are not limited to, aqueous alcohols, aqueous acetone, and combinations of the foregoing solvents. In one embodiment, the first solvent comprises isopropanol.

The third solution is then treated with a solid adsorbent to obtain a fourth solution and the solvent is removed from the fourth solution to obtain a third solid.

The third solid is then triturated as described above to obtain a fourth solid, wherein the fourth solid comprises greater than or equal to 99.9 weight percent 2-hydrocarbyl-3,3-bis(4-hydroxyaryl)phthalimidine of formula (I), based on the total weight of the fourth solid.

The final solids obtained in the above embodiments are highly purified monomers and comprise low levels of various impurities. In some embodiments, the final solid has an APHA yellowness index of less than or equal to 40, or more specifically, less than or equal to 20, or even more specifically, less than or equal to 10, as measured by spectrophotometry. In some embodiments, the final solid comprises less than or equal to 100, or more specifically, 50, parts per million by weight of residual solvent based on the total weight of the solid. In some other embodiments, the final solid comprises less than or equal to 1000, or more specifically, less than or equal to 500, parts per million by weight of phenolphthalein impurity based on the total weight of the solid. In yet other embodiments, the final solid comprises less than or equal to 100, or more specifically, 50, parts per million by weight of 2-hydrocarbyl-3,3-{(4-hydroxyaryl)(4-aminoaryl)}phthalimidine impurity based on the total weight of the solid. In some other embodiments, the final solid comprises less than or equal to 5, or more specifically, 1, parts per million by weight of iron based on the total weight of the solid, as measured by Inductively Coupled Plasma (ICP) spectrophotometer. In still other embodiments, the final solid comprises less than or equal to 5, or more specifically, 1, parts per million by weight of sodium based on the total weight of the solid, as measured by ICP spectrophotometer.

The final solids obtained above, including the exemplary 2-hydrocarbyl-3,3-bis(4-hydroxyaryl)phthalimidine materials, are commercially valuable monomers or comonomers for producing a variety of polymers and polymer compositions formed by reaction of the phenolic OH groups of the 2-hydrocarbyl-3,3-bis(4-hydroxyaryl)phthalimidines. Suitable polymers that can be produced are homopolymers and copolymers of a polycarbonate, a polyestercarbonate, a polyester, a polyesteramide, a polyimide, a polyetherimide, a polyamideimide, a polyether, a polyethersulfone, a polycarbonate—polyorganosiloxane block copolymer, a copolymer comprising aromatic ester, estercarbonate, and carbonate repeat units; and a polyetherketone. A suitable example of a copolymer comprising aromatic ester, estercarbonate, and carbonate repeat units is the copolymer produced by the reaction of a hydroxy-terminated polyester, such as the product of reaction of isophthaloyl chloride, and terephthaloyl chloride with resorcinol, with phosgene and an aromatic dihydroxy compound, such as bisphenol A.

In one embodiment, the polymer produced is a polycarbonate comprising repeating structural units of formula (VIII):

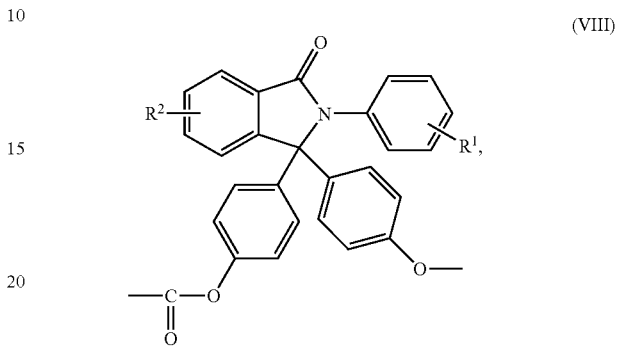

(VIII)

which are derived from 2-hydrocarbyl-3,3-bis(4-hydroxyaryl)phthalimidine. The C=O structural units are derived from a C=O donor such as phosgene or a carbonic acid diester. In one embodiment, the 2-hydrocarbyl-3,3-bis (4-hydroxyaryl)phthalimidine comprises less than or equal to 250 parts per million by weight of a 2-hydrocarbyl-3-{(4-hydroxyaryl)(4-aminoaryl)}phthalimidine impurity based on the total weight of the 2-hydrocarbyl-3,3-bis(4-hydroxyaryl) phthalimidine.

The polycarbonate may further comprise structural units derived from at least one other aromatic dihydroxy compound such as is represented by the general formula (IX):

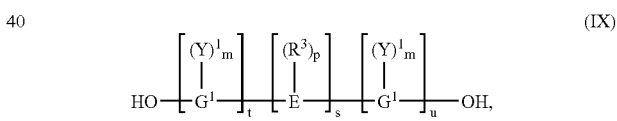

(IX)

wherein each $G^1$ is an independently aromatic group; E is selected from the group consisting of an alkylene group, an alkylidene group, a cycloaliphatic group, a sulfur-containing linkage group, a phosphorus-containing linkage group, an ether linkage group, a carbonyl group, a tertiary nitrogen group, and a silicon-containing linkage group; $R^3$ is a hydrogen or a hydrocarbyl group; $Y^1$ is independently selected from the groups consisting of a monovalent hydrocarbyl group, an alkenyl group, an allyl group, a halogen, an oxy group and a nitro group; each m is independently a whole number from zero through the number of positions on each respective $G^1$ available for substitution; p is a whole number from zero through the number of positions on E available for substitution; t is a natural number greater than or equal to one; s is either zero or one; and u is a whole number.

Suitable examples of E include cyclopentylidene, cyclohexylidene, 3,3,5-trimethylcyclohexylidene, methylcyclohexylidene, 2-[2.2.1]-bicycloheptylidene, neopentylidene, cyclopentadecylidene, cyclododecylidene, and adamantylidene; a sulfur-containing linkage such as sulfide, sulfoxide or sulfone, a phosphorus-containing linkage such as phosphinyl, phosphonyl, an ether linkage, a carbonyl group, a tertiary nitrogen group, and a silicon-containing linkage such as a silane or siloxy linkage.

In the aromatic dihydroxy comonomer compound shown in Formula (IX), when more than one $Y^1$ substituent is present, they may be the same or different. The same holds true for the $R^3$ substituent. Where "s" is zero in formula (IX) and "u" is not zero, the aromatic rings are directly joined with no intervening alkylidene or other bridge. The positions of the hydroxyl groups and $Y^1$ on the aromatic nuclear residues $G^1$ can be varied in the ortho, meta, or para positions and the groupings can be in vicinal, asymmetrical or symmetrical relationship, where two or more ring carbon atoms of the hydrocarbon residue are substituted with $Y^1$ and hydroxyl groups. In some embodiments, the parameters "t", "s", and "u" are each one; both $G^1$ radicals are unsubstituted phenylene radicals; and E is an alkylidene group such as isopropylidene. In particular embodiments, both $G^1$ radicals are p-phenylene, although both may be ortho- or meta-phenylene or one ortho- or meta-phenylene and the other para-phenylene.

Some illustrative, non-limiting examples of aromatic dihydroxy compounds of formula (IX) include the dihydroxy-substituted aromatic hydrocarbons disclosed by name or formula (generic or specific) in U.S. Pat. No. 4,217,438. Some particular examples of aromatic dihydroxy compound comonomers include, but are not limited to, Bisphenol A; resorcinol; $C_{1-3}$ alkyl-substituted resorcinols; 2,6-dihydroxy naphthalene; hydroquinone; 3-(4-hydroxyphenyl)-1,1,3-trimethylindan-5-ol; 1-(4-hydroxyphenyl)-1,3,3-trimethylindan-5-ol; 4,4'-dihydroxy-diphenyl; 1,1-bis(4'-hydroxy-3'methylphenyl)cyclohexane (DMBPC), 1,1-bis(3,5-dimethyl-4-hydroxyphenyl)cyclohexane; 4,4'-dihydroxydiphenylsulfone (BPS); bis(4-hydroxyphenyl) methane; and 2,2,2',2'-tetrahydro-3,3,3',3'-tetramethyl-1,1'-spirobi[1H-indene]-6,6'-diol. The most typical aromatic dihydroxy compound is Bisphenol A.

In some embodiments, an isosorbide comonomer can be used with the 2-hydrocarbyl-3,3-bis(4-hydroxyaryl)phthalimidine monomer to produce polycarbonate copolymers. Isosorbide, sometimes also called 1, 4:3,6-dianhydro-D-glucitol, is a rigid, chemically, and thermally stable aliphatic diol that tends to produce copolymers having higher glass transition temperatures, as compared to comonomer compositions which do not include isosorbide.

The carbonic acid diester described above has the general formula (X):

$$(ZO)_2C=O \quad\quad (X),$$

wherein each Z is independently an unsubstituted or substituted alkyl radical, or an unsubstituted or substituted aryl radical. Suitable examples of carbonic acid diesters include, but are not limited to, ditolyl carbonate, m-cresyl carbonate, dinaphthyl carbonate, diphenyl carbonate, diethyl carbonate, dimethyl carbonate, dibutyl carbonate, dicyclohexyl carbonate, and combinations of two or more carbonic acid diesters thereof. Diphenyl carbonate is widely used as a carbonic acid diester due to its low cost and ready availability on a commercial scale. If two or more of the carbonic acid diesters listed above are utilized, one of the carbonic acid diesters can be diphenyl carbonate.

Suitable carbonic acid diesters also include the group of "activated aromatic carbonates". As used herein, the term "activated aromatic carbonate" is defined as a diaryl carbonate that is more reactive than diphenyl carbonate in a transesterification reaction. Such activated aromatic carbonates can also be represented by formula (X), wherein each Z is an aryl radical having 6 to 30 carbon atoms. More specifically, the activated carbonates have the general formula (XI):

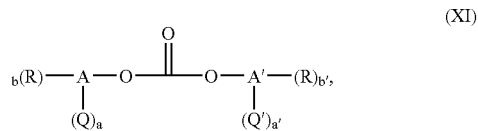

wherein Q and Q' are each independently an ortho-positioned activating group; A and A' are each independently aromatic rings which can be the same or different depending on the number and location of their substituent groups, and a and a' is zero to a whole number up to a maximum equivalent to the number of replaceable hydrogen groups substituted on the aromatic rings A and A' respectively, provided a+a' is greater than or equal to 1. R and R' are each independently substituent groups such as alkyl, substituted allyl, cycloalkyl, alkoxy, aryl, alkylaryl, cyano, nitro, or halogen. The term b is zero to a whole number up to a maximum equivalent to the number of replaceable hydrogen atoms on the aromatic ring A minus the number a, and the number b' is zero to a whole number up to a maximum equivalent to the number of replaceable hydrogen atoms on the aromatic ring A' minus the number a'. The number, type and location of R or R' on the aromatic ring is not intended to be limited unless they deactivate the carbonate and lead to a carbonate that is less reactive than diphenyl carbonate.

Non-limiting examples of suitable ortho-positioned activating groups Q and Q' include (alkoxycarbonyl)aryl groups, halogens, nitro groups, amide groups, sulfone groups, sulfoxide groups, or imine groups with structures indicated below:

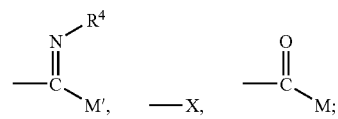

wherein X is halogen or $NO_2$; M and M' independently comprises N-diallyl, N-alkyl aryl, allyl, or aryl; and $R^4$ is alkyl or aryl.

Specific non-limiting examples of activated aromatic carbonates include bis(o-methoxycarbonylphenyl)carbonate, bis(o-chlorophenyl)carbonate, bis(o-nitrophenyl)carbonate, bis(o-acetylphenyl)carbonate, bis(o-phenylketonephenyl) carbonate, bis(o-formylphenyl)carbonate. Unsymmetrical combinations of these structures, wherein the substitution number and type on A and A' are different, are also contemplated. An exemplary structure for the activated aromatic carbonate is an ester-substituted diaryl carbonate having the formula (XII):

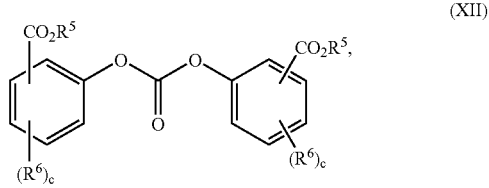

wherein $R^5$ is independently at each occurrence a $C_1$-$C_{20}$ allyl radical, $C_4$-$C_{20}$ cycloalkyl radical, or $C_4$-$C_{20}$ aromatic radical; $R^6$ is independently at each occurrence a halogen atom, cyano group, nitro group, $C_1$-$C_{20}$ allyl radical, $C_4$-$C_{20}$ cycloalkyl radical, $C_4$-$C_{20}$ aromatic radical, $C_1$-$C_{20}$ alkoxy radical, $C_4$-$C_{20}$ cycloalkoxy radical, $C_4$-$C_{20}$ aryloxy radical, $C_1$-$C_{20}$ alkylthio radical, $C_4$-$C_{20}$ cycloalkylthio radical, $C_4$-$C_{20}$ arylthio radical, $C_1$-$C_{20}$ alkylsulfinyl radical, $C_4$-$C_{20}$ cycloalkylsulfinyl radical, $C_4$-$C_{20}$ arylsulfinyl radical, $C_1$-$C_{20}$ alkylsulfonyl radical, $C_4$-$C_{20}$ cycloalkylsulfonyl radical, $C_4$-$C_{20}$ arylsulfonyl radical, $C_1$-$C_{20}$ alkoxycarbonyl radical, $C_4$-$C_{20}$ cycloalkoxycarbonyl radical, $C_4$-$C_{20}$ aryloxycarbonyl radical, $C_2$-$C_{60}$ alkylamino radical, $C_6$-$C_{60}$ cycloalkylamino radical, $C_5$-$C_{60}$ arylamino radical, $C_1$-$C_{40}$ alkylaminocarbonyl radical, $C_4$-$C_{40}$ cycloalkylaminocarbonyl radical, $C_4$-$C_{40}$ arylaminocarbonyl radical, or $C_1$-$C_{20}$ acylamino radical; and c is independently at each occurrence an integer 0-4. At least one of the substituents $CO_2R^5$ can be attached in the ortho position of formula (XII).

Examples of ester-substituted diaryl carbonates include, but are not limited to, bis(methylsalicyl)carbonate (CAS Registry No. 82091-12-1) (also known as BMSC or bis(o-methoxycarbonylphenyl)carbonate), bis(ethyl salicyl)carbonate, bis(propyl salicyl)carbonate, bis(butylsalicyl)carbonate, bis(benzyl salicyl)carbonate, bis(methyl 4-chlorosalicyl)carbonate and the like. In one embodiment, BMSC is used in melt polycarbonate synthesis due to its higher reactivity, lower molecular weight and higher vapor pressure.

The polycarbonates can comprise structural units indicative of the activated carbonate. These structural units may be end groups produced when activated carbonate fragments act as end capping agents or may be kinks introduced into the copolymer by incorporation of activated carbonate fragments.

A number of polymerization methods can be used for producing the polycarbonates. Suitable methods include, but are not limited to, a melt transesterification polymerization method, an interfacial polymerization method, and a bischloroformate polymerization method. Detailed polymerization methods are disclosed in U.S. Pat. No. 7,135,577, the entire contents of which are herein incorporated by reference.

In one embodiment, the melt transesterification polymerization method is generally carried out by combining a catalyst and a reactant composition to form a reaction mixture; and mixing the reaction mixture under reactive conditions for a time period effective to produce a polycarbonate product, wherein the reactant composition comprises a carbonic acid diester and the 2-hydrocarbyl-3,3-bis(4-hydroxyaryl)phthalimidine, wherein the 2-hydrocarbyl-3,3-bis(4-hydroxyaryl)phthalimidine comprises less than or equal to 100 parts per million of a solvent based on the total weight of the 2-hydrocarbyl-3,3-bis(4-hydroxyaryl)phthalimidine. In another embodiment, the 2-hydrocarbyl-3,3-bis(4-hydroxyaryl)phthalimidine comprises less than or equal to 1,000 parts per million of phenolphthalein based on the total weight of the 2-hydrocarbyl-3,3-bis(4-hydroxyaryl)phthalimidine. Need to include A,P-Impurity spec of 250 ppm and more specifically 50 ppm (Please check in all the embodiments).

During the manufacture of the polycarbonates by the melt transesterification method using the activated or unactivated carbonic acid diester, the amount of the carbonic acid diester comprises 0.8 to 1.30, or more specifically, 0.9 to 1.2 moles, based on one mole of the 2-hydrocarbyl-3,3-bis(4-hydroxyaryl)phthalimidine or any combination of the 2-hydrocarbyl-3,3-bis(4-hydroxyaryl)phthalimidine and at least one aromatic dihydroxy comonomer.

Suitable melt transesterification catalysts include alkali metal compounds, alkaline earth metal compounds, tetraorganoammonium compounds, tetraorganophosphonium compounds, and combinations of two or more of the foregoing catalysts.

The process disclosed herein can be used to prepare homopolycarbonate and copolycarbonates having a weight average molecular weight (Mw) of about 3,000 to about 150,000 and a glass transition temperature (Tg) of about 80° C. to about 300° C. The number average molecular weights (Mn) of the homopolycarbonate and copolycarbonates is from about 1,500 to about 75,000.

In the interfacial polymerization method, 2-hydrocarbyl-3,3-bis(4-hydroxyaryl)phthalimidine, with or without one or more comonomers, and phosgene are reacted in the presence of a tertiary amine and an aqueous base to produce said polycarbonate. Exemplary tertiary amines include, but are not limited to, trialkylamines. An exemplary trialkylamine is triethylamine. Suitable aqueous bases include, for example, the alkali metal hydroxides, such as sodium hydroxide. The interfacial method can be used for producing polycarbonates comprising structural units derived from 2-hydrocarbyl-3,3-bis(4-hydroxyaryl)phthalimidine, and having molecular weights greater than about 50,000, relative to polystyrene standard.

The interfacial method described above can be suitably adapted to produce polycarbonates through the intermediate formation of 2-hydrocarbyl-3,3-bis(4-hydroxyaryl)phthalimidine bischloroformate. This method is sometimes called the bischloroformate polymerization method. In one embodiment, the method comprises reacting a 2-hydrocarbyl-3,3-bis(4-hydroxyaryl)phthalimidine with phosgene in an organic solvent, and then reacting the bischloroformate either with a 2-hydrocarbyl-3,3-bis(4-hydroxyaryl)phthalimidine, or an aromatic dihydroxy compound in the presence of an acid acceptor and an aqueous base to form the polycarbonate.

The interfacial polymerization method and the bischloroformate polymerization method can be carried in a batch or a continuous mode using one or more reactor systems. To carry out the process in a continuous mode, one or more continuous reactors, such as for example, a tubular reactor can be used. In one embodiment, the continuous method comprises introducing into a tubular reactor system phosgene, at least one solvent (example, methylene chloride), at least one bisphenol, aqueous base, and optionally one or more catalysts (example, a trialkylamine) to form a flowing reaction mixture. The flowing mixture is then passed through the tubular reactor system until substantially all of the phosgene has been consumed. The resulting mixture is next treated with a mixture comprising an aqueous base, at least one end-capping agent, optionally one or more solvents, and at least one catalyst. The end-capped polycarbonate thus formed is continuously removed from the tubular reactor system. The process can be used for preparing end-capped polycarbonate oligomers (generally polycarbonates having a weight average molecular weight of less than or equal to 10,000 daltons) or polymers having a weight average molecular weight of greater than 10,000 daltons. The processes outlined hereinabove can also be suitably adapted, for example, to produce end-capped polycarbonates via the intermediate formation of a mixture comprising a bisphenol monochloroformate or a bisphenol bischloroformate.

Polymers, particularly polycarbonate homopolymers and copolymers comprising structural units derived from the high purity 2-hydrocarbyl-3,3-bis(4-hydroxyaryl)phthalimidine obtained above, for example para,para-PPPBP, have an APHA yellowness index of less than or equal to 40 as measured on a 3 millimeter thick plaque in accordance with ASTM D1925. In some embodiments, the APHA yellowness index is less than or equal to, 20, or more specifically, less than or equal to 10, or even more specifically, less than or equal to 5, or even more specifically, less than or equal to 2. Hence these polycarbonate polymers are useful for producing articles having a number of useful properties, such as a low residual color. The articles also exhibit excellent heat aging. Thus, extruded articles have low color values as measured by yellowness index (YI) even after heat aging, such as, for example, a YI of less than about 2 after heat aging in air at 155° C. to 160° C. for about 500 hours in one embodiment, and a YI of less than about 0.5 after heat aging in air at 120° C. for about 500 hours in another embodiment. The polycarbonate homopolymers and copolymers have high glass transition temperatures of higher than or equal to about 180° C. One of the unique properties of these polycarbonates, especially those that have glass transition temperatures of greater than or equal to about 180° C. is that during melt processing they exhibit a shear-thinning behavior. That is, the polymers have the ability to flow under an applied shear. Therefore, standard melt processing equipment used for BPA polycarbonates can advantageously be used for producing articles. The polycarbonates also have high transparency, as measured by percent light transmittance, of greater than or equal to about 84 percent, as measured by spectrophotometry. Moreover, the copolycarbonate is especially useful for articles that are made from a polymer having transparency and the other advantageous properties of a BPA homopolymer polycarbonate but with a significantly higher Tg. Lenses in applications where they are exposed to heat are a good example of such an application.

The polycarbonate compositions disclosed herein are particularly valuable for producing a variety of lenses suitable for diverse applications. In an embodiment, the lens comprises a polycarbonate, which comprises structural units of formula (VII) derived from a 2-hydrocarbyl-3,3-bis(4-hydroxyaryl)phthalimidine comprising less than or equal to 1,000, or more specifically, less than or equal to 250, or, even more specifically, less than or equal to 50 parts per million of a 2-hydrocarbyl-3,3-{(4-hydroxyaryl)(4-aminoaryl)}phthalimidine based on the total weight of the 2-hydrocarbyl-3, 3-bis(4-hydroxyaryl)phthalimidine; and a yellowness index of less than 40, as measured on a 3 millimeter thick plaque in accordance with ASTM D1925 in one embodiment, and less than 20 in another embodiment. Non-limiting examples of suitable articles include an automotive headlamp inner lens, an automotive headlamp outer lens, an automotive fog lamp lens, an automotive bezel, a medical device, a display device, electrical connectors, under the hood automotive parts, and projector lens. Examples of suitable display devices include a laptop computer screen, a liquid crystal display screen, and an organic light-emitting diode display screen.

The polycarbonates disclosed herein may also be combined with effective amounts of one or more of various types of additives selected from the group consisting of fillers, fire retardants, drip retardants, antistatic agents, UV stabilizers, heat stabilizers, antioxidants, plasticizers, dyes, pigments, colorants, processing aids, and mixtures thereof. These additives are known in the art, as are their effective levels and methods of incorporation. Effective amounts of the additives vary widely, but they are usually present in an amount up to about 50% or more by weight, based on the weight of the entire composition. Especially useful additives include hindered phenols, thio compounds and amides derived from various fatty acids. The typical amounts of these additives generally ranges up to about 2% total combined weight based on the total weight of the composition.

Methods for producing and purifying 2-hydrocarbyl-3,3-bis(4-hydroxyaryl)phthalimidine monomers and polycarbonates derived therefrom are further disclosed in the following non-limiting examples.

EXAMPLES

HPLC analysis was generally carried out by using a solution of about 50 milligrams of the sample dissolved in about 10 milliliters of methanol. The HPLC instrument was equipped with a C-18 (reverse phase) column maintained at a temperature of 40° C., and an ultraviolet detector capable of detecting components at a wavelength of 230 nanometers. A solvent mixture of acetonitrile, methanol and water (containing 0.02% phosphoric acid) of gradient elution was used. The flow rate was maintained at 1 milliliter per minute. Assay was computed by calculating the phenolphthalein content using suitable calibration for PP and the weight percent of all other impurities was calculated using the response factor of PPPBP. The purity of PPPBP was calculated by subtracting the amount of PP and "others" from 100.

Example 1

100.0 grams (g) (0.3141 mole) of phenolphthalein (having a purity of 99.7 weight percent), 117.0 g (1.25 mole) of aniline, and 32.8 milliliters (ml) of 35 wt % aqueous HCl (0.3141 mole) were combined in a 500 ml four neck round bottom flask fitted with an overhead stirrer, a nitrogen gas inlet, thermowell, and a condenser with Dean-Stark apparatus. A slow stream of nitrogen gas was continuously passed through the flask, and the reaction mixture was heated at 100 to 120° C. for 2 to 3 hours to remove the by-product water (approximately 28 ml). The reaction mixture was then heated at 155 to 160° C. for 22 to 24 hours and allowed to cool to 100 to 110° C. 250 ml of 10 wt % aqueous HCl was then added into the reaction mixture followed by stirring for 2 hours. A precipitate was formed, filtered out, washed 5 times with 100 ml of water (85° C.) (5×100 ml) until free from chloride, and dried, resulting in crude 2-phenyl-3,3-bis(4-hydroxyphenyl) phthalimidine.

The crude 2-phenyl-3,3-bis(4-hydroxyphenyl)phthalimidine (120 g) was then dissolved in 700 ml of 4 wt % aqueous NaOH solution, treated with 12 g of activated carbon for 1 hour and filtered. The activated carbon treatment was repeated 3 more times. The filtrate was acidified with 280 ml of 10 wt % aqueous HCl and heated to 70° C. for 1 hour to precipitate 2-phenyl-3,3-bis(4-hydroxyphenyl)phthalimidine, which was filtered out, washed with water until free from chloride and dried. The yield was 117.5 gm or 95%.

The precipitate comprising 2-phenyl-3,3-bis(4-hydroxyphenyl)phthalimidine was further purified using trituration and washing. The precipitate was triturated with 470 ml of methanol:water (90:10, v:v) and washed with 120 ml of methanol:water (90:10, v:v). Trituration was conducted at 70° C. for 120 minutes. After the methanol:water wash the solid washed with 120 ml of water. Final yield was 105 g with a purity of 99.94 w %.

Example 2

100.0 grams (g) (0.3141 mole) of phenolphthalein (having a purity of 99.7 weight percent), 117.0 g (1.25 mole) of aniline, and 32.8 milliliters (ml) of 35 wt % aqueous HCl (0.3141 mole) were combined in a 500 ml four neck round bottom flask fitted with an overhead stirrer, a nitrogen gas inlet, thermowell, and a condenser with Dean-Stark apparatus. A slow stream of nitrogen gas was continuously passed through the flask, and the reaction mixture was heated at 100 to 120° C. for 2 to 3 hours to remove the by-product water (approximately 28 ml). The reaction mixture was then heated at 155 to 160° C. for 22 to 24 hours and allowed to cool to 100 to 110° C. 250 ml of 10 wt % aqueous HCl was then added into the reaction mixture followed by stirring for 2 hours. A precipitate was formed, filtered out, washed 5 times with 100 ml of water (85° C.) (5×100 ml) until free from chloride, and dried, resulting in crude 2-phenyl-3,3-bis(4-hydroxyphenyl)phthalimidine.

The crude 2-phenyl-3,3-bis(4-hydroxyphenyl)phthalimidine (120 g) was then dissolved in 630 ml of 4 wt % aqueous NaOH solution. This solution was filtered. To the filtrate, a solution of 8.4 g NaOH in 66 ml water was added and stirred for 15 minutes. This reaction mixture was treated with 12 g of activated carbon for 1 hour and filtered. The activated carbon treatment was repeated 1 more time. The filtrate was acidified with 350 ml of 10 wt % aqueous HCl to precipitate 2-phenyl-3,3-bis(4-hydroxyphenyl)phthalimidine, which was filtered out, washed with water until free from chloride and dried. The yield was 120 g or 96%.

The precipitate comprising 2-phenyl-3,3-bis(4-hydroxyphenyl)phthalimidine was further purified using trituration and washing. The precipitate was triturated with 470 ml of methanol:water (90:10, v:v) and washed with 120 ml of methanol:water (90:10, v:v). Trituration was conducted at 70° C. for 120 minutes. After the methanol:water wash the solid washed with 120 ml of water. Final yield was 109 gm of PPPBP with purity of 99.91 w %.

Example 3

100.0 g (0.3141 mole) of phenolphthalein (having a purity of 99.7 weight percent), 117.0 g (1.25 mole) of aniline and 32.8 ml of 35 wt % aqueous HCl (0.3141 mole) were combined in a 1000 ml four neck round bottom flask fitted with a overhead stirrer, a nitrogen gas inlet, thermowell, and an condenser with Dean-Stark apparatus. A slow stream of nitrogen gas was continuously passed through the flask, and the reaction mixture was heated at 100 to 120° C. for 2 to 3 hours to remove the by-product water (approximately 21 ml). The reaction mixture was then heated at 155 to 160° C. for 22 to 24 hours and allowed to cool to 100 to 110° C. 700 ml of 4 wt % aqueous NaOH solution was then added into the reaction mixture followed by stirring for 2 hours. Free aniline was recovered by extracting the alkaline 2-phenyl-3,3-bis(4-hydroxyphenyl)phthalimidine solution with 200 ml (100 mlX2) of dichloroethane. The lower organic layer was separated out and aniline was recovered after distillation of solvent. The upper aqueous layer was transferred to a 1000 ml four neck round bottom flask and combined with 12 g of activated carbon, stirred for 1 hour, and filtered. Treatment with activated carbon was performed 3 more times. The filtrate was then acidified with 280 ml of 10 wt % aqueous HCl to precipitate 2-phenyl-3,3-bis(4-hydroxyphenyl)phthalimidine. The precipitate was filtered out, washed with water until free from chloride, and dried. The yield was 119.0 gm or 96%. The precipitate comprising 2-phenyl-3,3-bis(4-hydroxyphenyl)phthalimidine was further purified using trituration and washing. The precipitate was triturated with 470 ml of methanol:water (90:10, v:v) and washed with 120 ml of methanol:water (90:10, v:v). Trituration was conducted at 70° C. for 120 minutes. After the methanol:water wash the solid washed with 120 ml of water. Final purity was 99.95 wt % of 2-phenyl-3,3-bis(4-hydroxyphenyl)phthalimidine.

Example 4

100.0 g (0.3141 mole) of phenolphthalein (having a purity of 99.7 weight percent), 117.0 g (1.25 mole) of aniline and 32.8 ml of 35 wt % aqueous HCl (0.3141 mole) were combined in a 1000 ml four neck round bottom flask fitted with a overhead stirrer, a nitrogen gas inlet, thermowell, and an condenser with Dean-Stark apparatus. A slow stream of nitrogen gas was continuously passed through the flask, and the reaction mixture was heated at 100 to 120° C. for 2 to 3 hours to remove the by-product water (approximately 21 ml). The reaction mixture was then heated at 155 to 160° C. for 22 to 24 hours and allowed to cool to 100 to 110° C. 700 ml of 4 wt % aqueous NaOH solution was then added into the reaction mixture followed by stirring for 2 hours. Free aniline was recovered by extracting the alkaline 2-phenyl-3,3-bis(4-hydroxyphenyl)phthalimidine solution with 200 ml (100 mlX2) of dichloroethane. The lower organic layer was separated out and aniline was recovered after distillation of solvent. The upper aqueous layer was filtered and transferred to a 1000 ml four neck round bottom flask. To this was added a solution of 5.6 gm NaOH in 50 ml water and stirred for 15 minutes. This reaction mass was treated with 12 g of charcoal, stirred for 1 hour, and filtered to remove charcoal. Treatment with charcoal was repeated 1 more time. The filtrate was then acidified with 280 ml of 10 wt % aqueous HCl to precipitate 2-phenyl-3,3-bis(4-hydroxyphenyl)phthalimidine. The precipitate was filtered out, washed with water until free from chloride, and dried. The yield was 119.0 gm or 96%. The precipitate comprising 2-phenyl-3,3-bis(4-hydroxyphenyl)phthalimidine was further purified using trituration and washing. The precipitate was triturated with 470 ml of methanol:water (90:10, v:v) and washed with 120 ml of methanol:water (90:10, v:v). Trituration was conducted at 70° C. for 120 minutes. After the methanol:water wash the solid washed with 120 ml of water.

Example 5

A mixture of 16.57 g of phenolphthalein (having a purity of 97.31 weight percent), 19.38 ml of aniline, and 5.79 ml of 35 wt % HCl was heated at 144 to 146° C. for 45 to 48 hours. The reaction mixture was then quenched with 50 ml of water and 25 ml of 10 wt % HCl and stirred for 1 hour at 100° C. The reaction mixture was filtered and dried overnight at 120° C. 22.0 g of crude 2-phenyl-3,3-bis(4-hydroxyphenyl)phthalimidine was obtained.

20.0 g of 2-phenyl-3,3-bis(4-hydroxyphenyl)phthalimidine was dissolved in aqueous base (4.2 g of NaOH in 96 ml of water) and the mixture was stirred at room temperature for 1 hour, then filtered to remove the insolubles. To the filtrate was added 1.4 g of NaOH in 11 ml of water. The mixture was stirred for 15 minutes and 2.0 g of charcoal was added and the mixture was stirred for 1 hour and filtered. The charcoal treatment was repeated two more times. Following the last charcoal treatment the filtrate was acidified with 16.66 ml of 35 wt % HCl in 88.6 ml of water. The precipitated solid was filtered and dried overnight at 110° C. 15.0 g of this material was triturated with 60 ml of methanol:water (90:10, v:v) for 1 hour at reflux temperature. The mixture was filtered and the solid was dried. The solid (14.0 g) was triturated as second time in 56 ml of methanol:water (90:10, v:v). The mixture was filtered and 5.0 g of the solid was triturated in 15 ml of acetone:water (80:20, v:v) at room temperature for 3 hours. The mixture was filtered and the solid was dried overnight at 105° C. The solid had an APHA of 34 and a purity of 99.93 wt %.

Example 6

A mixture of 88.0 g of phenolphthalein (having a purity of 98.7 weight percent), 102.96 ml of aniline, and 29.04 ml of 35 wt % HCl was heated at 144 to 146° C. for 45 to 48 hours. The reaction mixture was then quenched with 264 ml of water and 135 ml of 35 wt % HCl and stirred for 1 hour at 100° C. The reaction mixture was filtered and dried overnight at 120° C. 105.6 g of crude 2-phenyl-3,3-bis(4-hydroxyphenyl)phthalimidine was obtained.

56.0 g of 2-phenyl-3,3-bis(4-hydroxyphenyl)phthalimidine was dissolved in aqueous base (11.76 g of NaOH in 268.8 ml of water) and the mixture was stirred at room temperature for 1 hour, then filtered to remove the insolubles. To the filtrate was added 3.92 g of NaOH in 30.8 ml of water. The mixture was stirred for 15 minutes and 5.6 g of charcoal was added and the mixture was stirred for 1 hour and filtered. The charcoal treatment was repeated two more times. Following the last charcoal treatment the filtrate was acidified with 46.6 ml of 35 wt % HCl in 248 ml of water. The precipitated solid was filtered and dried overnight at 110° C. 10.0 g of this material was triturated with 40 ml of methanol:water (90:10, v:v) for 1 hour at reflux temperature. The mixture was filtered and the solid was dried. 5.0 g of the dried solid was triturated in 15 ml of acetone:water (80:20, v:v) at room temperature for 3 hours. The mixture was filtered and the solid was dried overnight at 105° C. The solid had an APHA of 31 and a purity of 99.94 wt %.

Example 7

A mixture of 75 g of phenolphthalein (having a purity of 99.4 weight percent), 87.75 ml of aniline, and 24.75 ml of 35 wt % HCl was heated at 144 to 146° C. for 45 to 48 hours. The reaction mixture was then quenched with 225 ml of water and 115 ml of 35 wt % HCl and stirred for 1 hour at 100° C. The reaction mixture was filtered and dried overnight at 120° C. 87.8 g of crude 2-phenyl-3,3-bis(4-hydroxyphenyl)phthalimidine was obtained.

60.0 g of 2-phenyl-3,3-bis(4-hydroxyphenyl)phthalimidine was dissolved in aqueous base (12.6 g of NaOH in 288 ml of water) and the mixture was stirred at room temperature for 1 hour, then filtered to remove the insolubles. To the filtrate was added 4.2 g of NaOH in 33 ml of water. The mixture was stirred for 15 minutes and 6.0 g of charcoal was added and the mixture was stirred for 1 hour and filtered. The charcoal treatment was repeated two more times. Following the last charcoal treatment the filtrate was acidified with 50 ml of 35 wt % HCl in 266 ml of water. The precipitated solid was filtered and dried overnight at 110° C. 20.0 g of this material was triturated with 80 ml of methanol:water (90:10, v:v) for 1 hour at reflux temperature. The mixture was filtered and the solid was dried. 5.0 g of the dried solid was triturated in 15 ml of acetone:water (80:20, v:v) at room temperature for 3 hours. The mixture was filtered and the solid was dried overnight at 105° C. The solid had an APHA of 20 and a purity of 99.94 wt %.

Examples 8 and 9

50 g of crude 2-phenyl-3,3-bis(4-hydroxyphenyl)phthalimidine was dissolved in 650 ml of isopropyl alcohol (IPA). 5 g (10 wt %) of silica was added and stirred at 80° C. for 1 hour. The mixture was then filtered hot and the filtrate was concentrated by evaporation of 450 ml of IPA, leaving 200 ml of IPA in the mixture until 4 volumes of solvent remained. Water was added according to the ratio shown in Table 1 and refluxed for 1 hour. The resulting solid was isolated by filtration and further treated with water at 85° C. for 1 hour. The mixture was filtered, the solid washed with water, and dried in an oven at 120° C. The solid was tested for iron content, sodium content and APHA. Results are shown in Table 1. The Fe and Na results are in parts by weight of Fe or Na per billion parts by weight of solid. Untreated 2-phenyl-3,3-bis(4-hydroxyphenyl)phthalimidine has approximately 5 ppm of Fe and 10 ppm of Na.

TABLE 1

| Example | IPA:water | Fe | Na | APHA |
|---------|-----------|-----|-----|------|
| 8 | 50:50 | 239 | 566 | 14 |
| 9 | 70:30 | 555 | 400 | 9 |

Examples 10-16

50 g of crude 2-phenyl-3,3-bis(4-hydroxyphenyl)phthalimidine was triturated with 5 or 10 wt % HCl at 70° C. for 4 hours. The resulting solid washed with water and triturated with methanol:water (90:10, v:v) once or twice as shown in Table 2. The resulting solid washed with 90° C. water and dried at 120° C. The solid was tested for iron content, sodium content and APHA. Results are shown in Table 2. The Fe and Na results are in parts by weight of Fe or Na per billion parts by weight of solid.

TABLE 2

| Example | Conditions | Fe | Na | APHA |
|---------|------------|-----|-----|------|
| 10 | 10 wt % HCl; 2 methanol:water triturations | 121 | <20 | 11 |
| 11 | 10 wt % HCl; 1 methanol:water trituration | 596 | 543 | 19 |
| 12 | 10 wt % HCl; 2 methanol:water triturations | 950 | 331 | 13 |
| 13 | 10 wt % HCl; 1 methanol:water trituration | 277 | 137 | 21 |
| 14 | 10 wt % HCl; 2 methanol:water triturations | 334 | 646 | 10 |
| 15 | 5 wt % HCl; 1 methanol:water trituration | 178 | 437 | 18 |
| 16 | 5 wt % HCl; 2 methanol:water trituration | 163 | 236 | 16 |

Comparative Example A 100 g phenolphthalein material having a purity of less than 96 wt % was used to prepare clear grade 2-phenyl-3,3-bis(4-hydroxyphenol)phthalimidine. The molar ratio of aniline:phenolphthalein:HCl in the reaction mixture was 4:1:1. The reaction was quenched with 10 wt. % HCl aqueous solution till pH 2 and filtered to obtain crude 2-phenyl-3,3-bis(4-hydroxyphenol)phthalimidine. The crude 2-phenyl-3,3-bis(4-hydroxyphenol)phthalimidine washed with water at a temperature of 25° C. and filtered to obtain a washed solid. The washed solid (125 grams) was dissolved in 700 ml of 4 wt. % NaOH aqueous solution and filtered.

The first solution was treated with 12 gm (10 wt. %) activated carbon 4 times to obtain a solution. The solution was acidified using 280 ml of 10 wt. % HCl aqueous solution (pH of 1 to 3) to precipitate 2-phenyl-3,3-bis(4-hydroxyphenyl)phthalimidine. The precipitated 2-phenyl-3,3-bis(4-hydroxyphenyl)phthalimidine was isolated by filtration. The precipitated 2-phenyl-3,3-bis(4-hydroxyphenyl)phthalimidine was then triturated using methanol:water (90:10, v:v) as triturating agent to obtain a slurry. The slurry was filtered to further remove impurities. The above trituration process was repeated 3 more times to obtain 87 g of purified 2-phenyl-3,3-bis(4-hydroxyphenol)phthalimidine solid.

The purified 2-phenyl-3,3-bis(4-hydroxyphenyl)phthalimidine solid comprised 99.93 weight percent 2-phenyl-3,3-bis(4-hydroxyphenyl)phthalimidine and had an APHA of 300.

Example 17 and Comparative Examples B and C

In Example 17, 2-phenyl-3,3-bis(4-hydroxyphenyl)phthalimidine monomer having a purity of at least 99.9 weight percent was used. 10-30 wt % of 2-phenyl-3,3-bis(4-hydroxyphenyl)phthalimidine based on the total weight of the monomer was used with bisphenol A to make a polycarbonate copolymer. Polymerization was performed by melt polymerization. The properties of the polymer obtained are summarized in Table 3.

In Comparative Examples B and C, 2-phenyl-3,3-bis(4-hydroxyphenyl)phthalimidine monomers having lower purities (95 and 96 weight percent, respectively) were used with bisphenol A to make polycarbonate polymers using the same polymerization conditions as Example 5. The properties of the polymers obtained are also summarized in Table 3.

As can be seen from the data in Table 3, the polymer obtained from clear grade monomer (Ex. 17) has a weight average molecular weight (Mw) of 29,362 and a number average molecular weight (Mn) of 14,696. The polydispersity index (PDI) is 2.00 and the glass transition temperature (Tg) is 197.97° C. The 5 weight percent loss temperature, the 10 weight percent loss temperature, and the 50 weight percent loss temperature are 421.6° C., 451.65° C., and 496.7° C., respectively.

In contrast, polymers obtained from lower purity monomers (CE. b and CE. c) have higher polydispersity indexes and lower weight loss temperatures.

While the disclosure has been described with reference to certain particular embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from essential scope thereof. Therefore, it is intended that the disclosure not be limited to the particular embodiment disclosed as the best mode contemplated for carrying out this invention, but that the disclosure will include all embodiments falling within the scope of the appended claims.

The invention claimed is:

1. A method for producing 2-hydrocarbyl-3,3-bis(4-hydroxyaryl)phthalimidine comprising:

reacting a phenolphthalein material and a primary hydrocarbyl amine in the presence of an acid catalyst to form a reaction mixture comprising 2-hydrocarbyl-3,3-bis(4-hydroxyaryl)phthalimidine, wherein the phenolphthalein material comprises greater than or equal to 99 weight percent phenolphthalein, based on the total weight of the phenolphthalein material;

quenching the reaction mixture and treating the quenched reaction mixture to obtain a first solution;

filtering the first solution;

adding base to the filtered first solution to obtain a second solution;

treating the second solution two or more times with a solid adsorbent to obtain a third solution;

acidifying the third solution to precipitate a second solid;

isolating and washing the second solid;

triturating the second solid in a triturating solvent to obtain a third solid, wherein the third solid comprises greater than or equal to 99.9 weight percent 2-hydrocarbyl-3,3-bis(4-hydroxyaryl)phthalimidine, based on the total

TABLE 3

| Ex. | PPPBP Purity (%) | Mw | Mn | PDI | Tg (° C.) | 5 wt. % loss temperature (° C.) | 10 wt. % loss temperature (° C.) | 50 wt. % loss temperature (° C.) |
|---|---|---|---|---|---|---|---|---|
| 17 | 99.9 | 29362 | 14696 | 2.00 | 197.97 | 421.55 | 451.65 | 496.68 |
| CE. B | 95 | 32090 | 9281 | 3.458 | 190.98 | 400–454, completely degrades | | |
| CE. C | 96 | 75236 | 13453 | 5.590 | 197.33 | | 412.58 | | weight of the third solid; and wherein the 2-hydrocarbyl-3,3-bis(4-hydroxyaryl)phthalimidine is of formula (I):

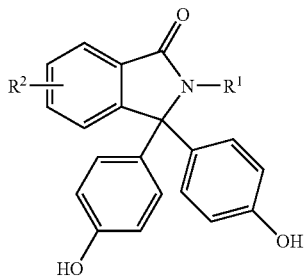

wherein $R^1$ is selected from the group consisting of a hydrogen and a hydrocarbyl group, and $R^2$ is selected from the group consisting of a hydrogen, a hydrocarbyl group, and a halogen.

2. The method of claim 1 wherein quenching is performed with an acid and forms a slurry comprising a precipitate and treating the quenched reaction mixture comprises:
   filtering the slurry to isolate the precipitate; and
      washing the precipitate with water to obtain a washed precipitate, wherein the water has a temperature of 25 to 90° C. to obtain a first solid;
      dissolving the first solid in an aqueous basic solution to obtain the first solution.

3. The method of claim 2, wherein the acid used in quenching is aqueous hydrochloric acid.

4. The method of claim 1, wherein the quenching is performed with aqueous base and forms a biphasic system and treating the quenched reaction mixture comprises:
   adding an organic solvent to the biphasic system;
   removing the basic layer of the biphasic system after adding the organic solvent to obtain a first solution.

5. The method of claim 1, wherein the phenolphthalein material comprises greater than or equal to 99.6 weight percent phenolphthalein, based on the total weight of the phenolphthalein material.

6. The method of claim 1, wherein the basic aqueous solution is an aqueous solution of sodium hydroxide.

7. The method of claim 1, wherein the solid adsorbent comprises an activated carbon.

8. The method of claim 1, wherein the third solid has an APHA yellowness index of less than or equal to 40, as measured by Spectrophotometer.

9. The method of claim 1, wherein the third solid comprises less than or equal to 50 parts per million by weight of residual solvent based on the total weight of the third solid.

10. The method of claim 1, wherein the third solid comprises less than or equal to 500 parts per million by weight of phenolphthalein based on the total weight of the fourth solid.

11. The method of claim 1, wherein the third solid comprises less than or equal to 50 parts per million by weight of 2-hydrocarbyl-3,3-{(4-hydroxyaryl)(4-aminoaryl)}phthalimidine based on the total weight of the third solid.

12. The method of claim 1, wherein the acidifying the third solution is carried out with 5 wt. % HCl aqueous solution at a temperature of 50 to 100° C. for a time period of 1 to 4 hours.

13. The method of claim 12, wherein the third solid comprises less than or equal to 1 part per million by weight of iron, based on the total weight of the third solid, as measured by Inductively Coupled Plasma spectrophotometer.

14. The method of claim 12, wherein the third solid comprises less than or equal to 1 part per million by weight of sodium, based on the total weight of the fourth solid, as measured by Inductively Coupled Plasma spectrophotometer.

15. A method for producing 2-hydrocarbyl-3,3-bis(4-hydroxyaryl)phthalimidine comprising:
   reacting a phenolphthalein material and a primary hydrocarbyl amine in the presence of an acid catalyst to form a reaction mixture comprising 2-hydrocarbyl-3,3-bis(4-hydroxyaryl)phthalimidine, wherein the phenolphthalein material comprises greater than or equal to 99 weight percent phenolphthalein, based on the total weight of the phenolphthalein material;
   quenching the reaction mixture and treating the quenched reaction mixture to obtain a first solution;
   filtering the first solution;
   adding base to the filtered first solution to obtain a second solution;
   treating the second solution two or more times with a first solid adsorbent to obtain a third solution;
   acidifying the third solution to precipitate a second solid;
   isolating and washing the second solid;
   dissolving the second solid in a first solvent to obtain a fourth solution;
   treating the fourth solution with a second solid adsorbent to obtain a fifth solution;
   removing solvent from the fifth solution to obtain a third solid;
   triturating the third solid in a triturating solvent to obtain a fourth solid, wherein the fourth solid comprises greater than or equal to 99.9 weight percent 2-hydrocarbyl-3,3-bis(4-hydroxyaryl)phthalimidine, based on the total weight of the fourth solid; and wherein the 2-hydrocarbyl-3,3-bis(4-hydroxyaryl)phthalimidine is of formula (I):

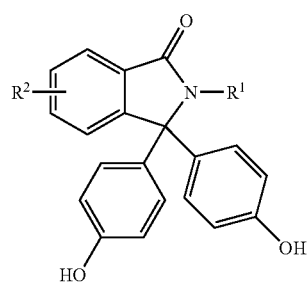

wherein $R^1$ is selected from the group consisting of a hydrogen and a hydrocarbyl group, and $R^2$ is selected from the group consisting of a hydrogen, a hydrocarbyl group, and a halogen.

16. The method of claim 15, wherein quenching is performed with an acid and forms a slurry comprising a precipitate and treating the quenched reaction mixture comprises:
   filtering the slurry to isolate the precipitate; and
      washing the precipitate with water to obtain a washed precipitate, wherein the water has a temperature of 25 to 90° C. to obtain a first solid;
      dissolving the first solid in an aqueous basic solution to obtain the first solution.

17. The method of claim 16, wherein the acid used in quenching is aqueous hydrochloric acid.

18. The method of claim 15, wherein the quenching is performed with aqueous base and forms a biphasic system and treating the quenched reaction mixture comprises:
adding an organic solvent to the biphasic system;
removing the basic layer of the biphasic system after adding the organic solvent to obtain the first solution.

19. The method of claim 15, wherein the fourth solid comprises less than or equal to 1 part per million by weight of iron, based on the total weight of the fourth solid, as measured by Inductively Coupled Plasma spectrophotometer.

20. The method of claim 15, wherein the fourth solid comprises less than or equal to 1 part per million by weight of sodium, based on the total weight of the fourth solid, as measured by Inductively Coupled Plasma spectrophotometer.

21. The method of claim 15, wherein the second solid adsorbent comprises silica or alumina.

22. A method for producing 2-hydrocarbyl-3,3-bis(4-hydroxyaryl)phthalimidine comprising:
reacting a phenolphthalein material and a primary hydrocarbyl amine in the presence of an acid catalyst to form a reaction mixture comprising 2-hydrocarbyl-3,3-bis(4-hydroxyaryl)phthalimidine, wherein the phenolphthalein material comprises greater than or equal to 99 weight percent phenolphthalein, based on the total weight of the phenolphthalein material;
quenching the reaction mixture and treating the quenched reaction mixture to obtain a first solution;
treating the first solution four or more times with a solid adsorbent to obtain a second solution;
acidifying the second solution and heating the mixture at a temperature of 50 to 100° C. to precipitate a second solid;
isolating the second solid;
triturating the second solid in a triturating solvent to obtain a third solid, wherein the third solid comprises greater than or equal to 99.9 weight percent 2-hydrocarbyl-3,3-bis(4-hydroxyaryl)phthalimidine, based on the total weight of the third solid; and wherein the 2-hydrocarbyl-3,3-bis(4-hydroxyaryl)phthalimidine is of formula (I):

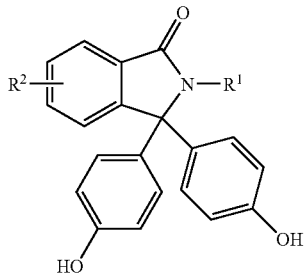

(I)

wherein $R^1$ is selected from the group consisting of a hydrogen and a hydrocarbyl group, and $R^2$ is selected from the group consisting of a hydrogen, a hydrocarbyl group, and a halogen.

23. The method of claim 22, wherein quenching is performed with an acid and forms a slurry comprising a precipitate and treating the quenched reaction mixture comprises:
filtering the slurry to isolate the precipitate; and
washing the precipitate with water to obtain a washed precipitate, wherein the water has a temperature of 25 to 90° C. to obtain a first solid;
dissolving the first solid in an aqueous basic solution to obtain the first solution.

24. The method of claim 23, wherein the acid used in quenching is aqueous hydrochloric acid.

25. The method of claim 22, wherein the quenching is performed with aqueous base and forms a biphasic system and treating the quenched reaction mixture comprises:
adding an organic solvent to the biphasic system;
removing the basic layer of the biphasic system after adding the organic solvent to obtain a first solution.

26. A method for producing 2-hydrocarbyl-3,3-bis(4-hydroxyaryl)phthalimidine comprising:
reacting a phenolphthalein material and a primary hydrocarbyl amine in the presence of an acid catalyst to form a reaction mixture comprising 2-hydrocarbyl-3,3-bis(4-hydroxyaryl)phthalimidine, wherein the phenolphthalein material comprises greater than or equal to 99 weight percent phenolphthalein, based on the total weight of the phenolphthalein material;
quenching the reaction mixture and treating the quenched reaction mixture to obtain a first solution;
treating the first solution with a solid adsorbent four or more times to obtain a second solution;
acidifying the second solution and heating at a temperature of 50 to 100° C. to precipitate a second solid;
isolating the second solid;
dissolving the second solid in a solvent to obtain a third solution;
treating the third solution with a solid adsorbent to obtain a fourth solution;
removing solvent from the fourth solution to obtain a third solid;
triturating the third solid in a triturating solvent to obtain a fourth solid, wherein the fourth solid comprises greater than or equal to 99.9 weight percent 2-hydrocarbyl-3,3-bis(4-hydroxyaryl)phthalimidine, based on the total weight of the fourth solid; and wherein the 2-hydrocarbyl-3,3-bis(4-hydroxyaryl)phthalimidine is of formula (I):

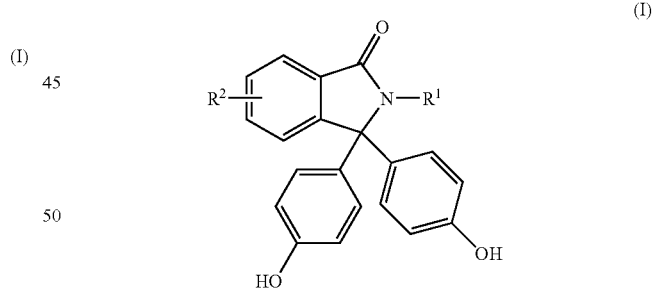

(I)

wherein $R^1$ is selected from the group consisting of a hydrogen and a hydrocarbyl group, and $R^2$ is selected from the group consisting of a hydrogen, a hydrocarbyl group, and a halogen.

27. A method for producing 2-hydrocarbyl-3,3-bis(4-hydroxyaryl)phthalimidine comprising:
reacting a phenolphthalein material and a primary hydrocarbyl amine in the presence of an acid catalyst to form a reaction mixture comprising 2-hydrocarbyl-3,3-bis(4-hydroxyaryl)phthalimidine, wherein the phenolphthalein material comprises greater than or equal to 97 weight percent phenolphthalein, based on the total weight of the phenolphthalein material;

quenching the reaction mixture and treating the quenched reaction mixture to obtain a first solid;

dissolving the first solid in an aqueous base to obtain a first solution;

filtering the first solution;

adding 0.5 to 2.5 moles of a base per mole of the first solid to the filtered first solution to obtain a second solution;

treating the second solution two or more times with a solid adsorbent to obtain a third solution;

acidifying the third solution to precipitate a second solid;

isolating and washing the second solid;

triturating the second solid in a first triturating solvent to obtain a third solid;

triturating the third solid with a second triturating solvent system to get a fourth solid wherein the fourth solid comprises greater than or equal to 99.9 weight percent 2-hydrocarbyl-3,3-bis(4-hydroxyaryl)phthalimidine, based on the total weight of the fourth solid; and wherein the 2-hydrocarbyl-3,3-bis(4-hydroxyaryl)phthalimidine is of formula (I):

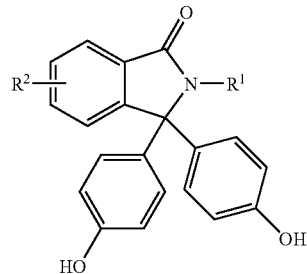

(I)

wherein $R^1$ is selected from the group consisting of a hydrogen and a hydrocarbyl group, and $R^2$ is selected from the group consisting of a hydrogen, a hydrocarbyl group, and a halogen.

* * * * *